United States Patent [19]

Brighton

[11] Patent Number: 4,487,834

[45] Date of Patent: Dec. 11, 1984

[54] ELECTRICAL STIMULATION OF ARTICULAR CHONDROCYTES

[75] Inventor: Carl T. Brighton, Malvern, Pa.

[73] Assignee: Biolectron, Inc., Hackensack, N.J.

[21] Appl. No.: 419,432

[22] Filed: Sep. 17, 1982

[51] Int. Cl.$^3$ .................. C12N 13/00; C12N 5/00
[52] U.S. Cl. ........................... 435/173; 435/240; 128/804
[58] Field of Search ............ 435/173, 240, 211; 128/419 F, 804

[56] References Cited

U.S. PATENT DOCUMENTS

| | | | |
|---|---|---|---|
| 3,336,220 | 7/1964 | Neidl ............................ | 435/173 |
| 3,842,841 | 10/1974 | Brighton et al. ............... | 128/419 R |
| 3,893,462 | 7/1975 | Manning ........................ | 128/421 |

FOREIGN PATENT DOCUMENTS 2841455  4/1980  Fed. Rep. of Germany ...... 435/173

OTHER PUBLICATIONS

Rodan et al., DNA Synthesis in Cartilage Cells is Stimulated by Osc. Electric Fields, Science, vol. 199, 2-10-78, pp. 690–692.

Y. C. Choi, G. M. Morris, F. S. Lee and L. Sokoloff, The Effect of Serum on Monolayer Cell Culture of Mammalian Articular Chondrocytes, Jun. 5, 1979, pp. 105–112.

J. B. Rich, R. C. Lee and M. B. Mathews, In vitro Electrical Stimulation of Chondrocyte Synthetic Response, Nov. 9–11, 1981, p. 32.

*Primary Examiner*—Steven Weinstein
*Assistant Examiner*—Marianne Minnick
*Attorney, Agent, or Firm*—Brumbaugh, Graves, Donohue & Raymond

[57] ABSTRACT

Cell development in articular chondrocytes is enhanced by subjecting them to an alternating current field having a frequency of about 60/khz and a current density in the order of 30–40 $\mu$amps/cm$^2$.

4 Claims, 5 Drawing Figures

ELECTRICAL STIMULATION OF ARTICULAR CHONDROCYTES

The present invention relates to a method for modulating a predetermined cellular response in mammalian articular chondrocytes by electrical stimulation. More particularly, it relates to a novel method in which the in vitro effects of high homologous serum concentrations on the incorporation of thymidine by mammalian articular chondrocytes and of low serum concentrations on sulphate incorporation are enhanced by electrical stimulation.

DESCRIPTION OF THE PRIOR ART

In recent years it has been discovered that growth in musculoskeletal system cell types responds favorably to electrical stimulation. For example, it has been found that healing of a bone fracture can be enhanced by supplying constant current to electrodes positioned invasively at the fracture site, as disclosed in U.S. Pat. No. 3,842,841. Good results have also been achieved with high frequency alternating current signals fed to electrodes non-invasively applied to the skin of a living body, as disclosed in the copending application of Joseph L. Lawrence and Carl T. Brighton Ser. No. 168,500, filed July 14, 1980. It has also been proposed to treat bone fractures by exposing them to magnetic fields generated by coils supplied with periodically varying current and positioned non-invasively in the vicinity of a fracture site, as shown in U.S. Pat. No. 3,893,462 to Manning.

Choi et al., in Conn. Tiss. Res., 7:105 1980, have shown that high homologous serum concentrations preferentially stimulate the incorporation of thymidine by mammalian articular chondrocytes, while low serum concentrations selectively enhance sulphate incorporation. It is an object of this invention to provide a novel method for further enhancing these in vitro effects in a statistically significant manner.

BRIEF STATEMENT OF THE INVENTION

According to the invention, mammalian articular chondrocytes in both high homologous serum concentrations and in low serum concentrations are subjected to an alternating electrical field of sine waveform at a frequency of about 60 KHz and a current of preferably about 30–40 microamperes/cm$^2$ (rms). Surprisingly, it has been found that treatment of the chondrocytes in this manner further enhances the in vitro effects previously observed by Choi et al.

The invention may be better understood from the following detailed description taken in conjunction with the accompanying drawings, in which:

FIG. 1 is a schematic diagram of a simple test apparatus for subjecting articular chondrocytes to electrical stimulation in vitro according to the invention;

FIGS. 2 and 3 are dose response curves for articular chondrocyte pellets in 1% and 10% newborn calf sera (NBCS) respectively, in which relative $^3$H thymidine incorporation is plotted against applied external voltage; and FIGS. 4 and 5 are typical dose response curves for articular chondrocyte pellets in 1% and 10% newborn calf sera (NBCS), respectively, in which relative $^{35}$S-sulphate incorporation is plotted against applied external voltage.

DESCRIPTION OF A PREFERRED EMBODIMENT

Figure 1:
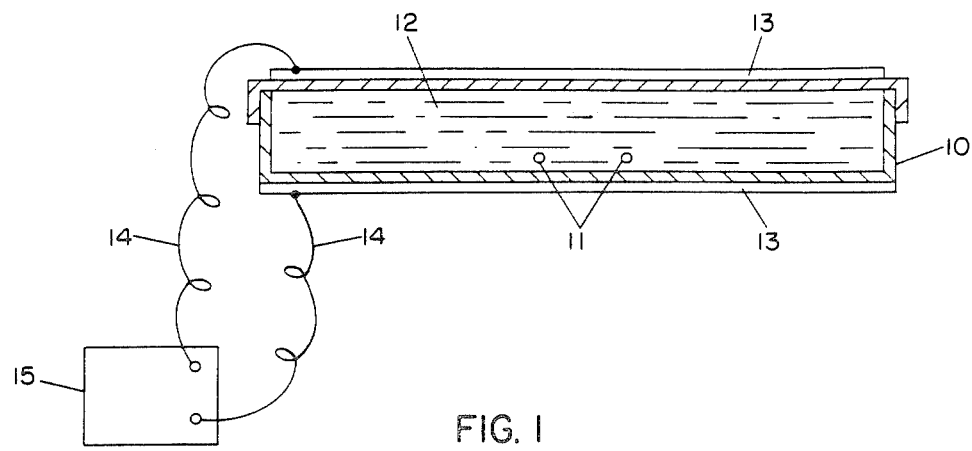
Figure 2:
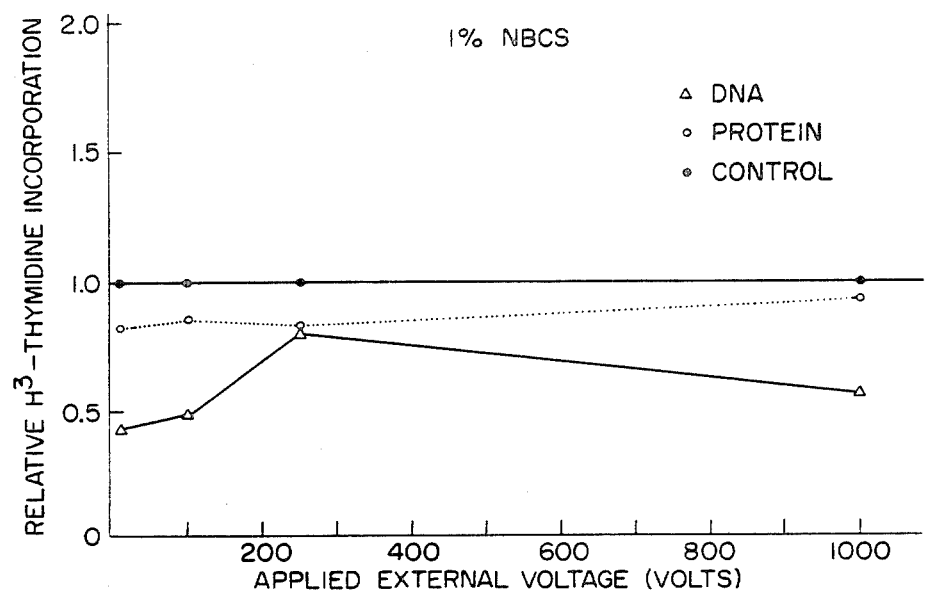
Figure 3:
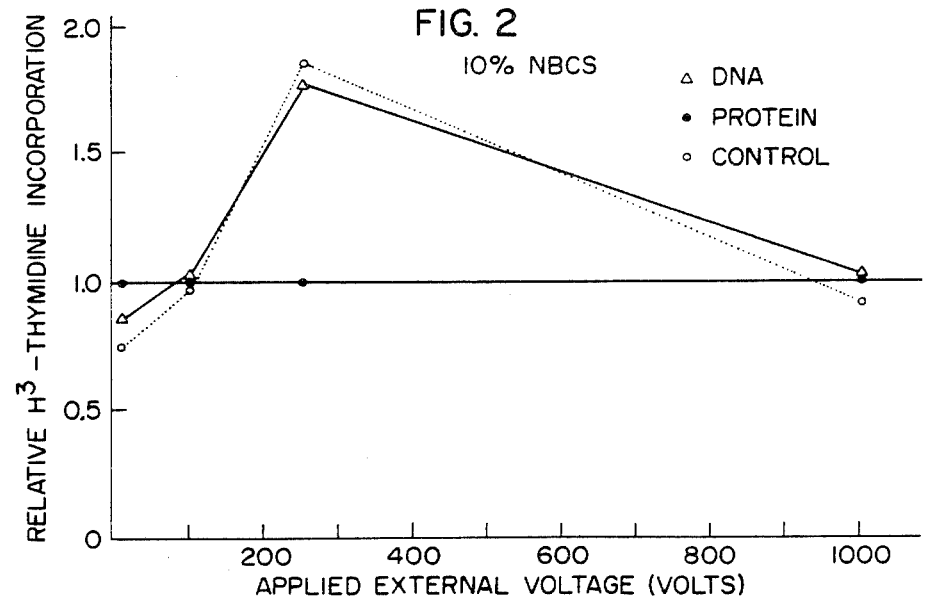
Figure 4:
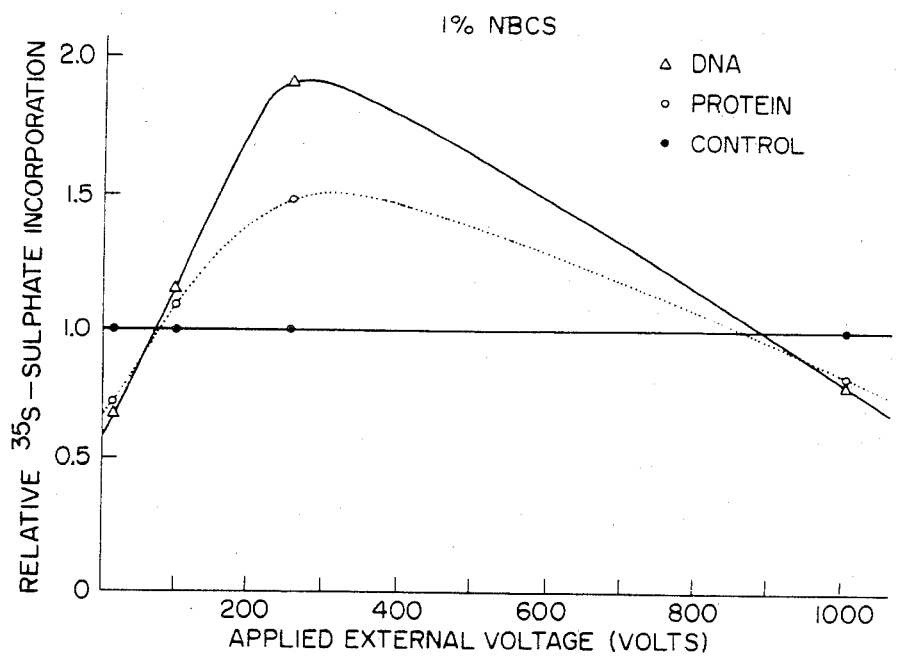
Figure 5:
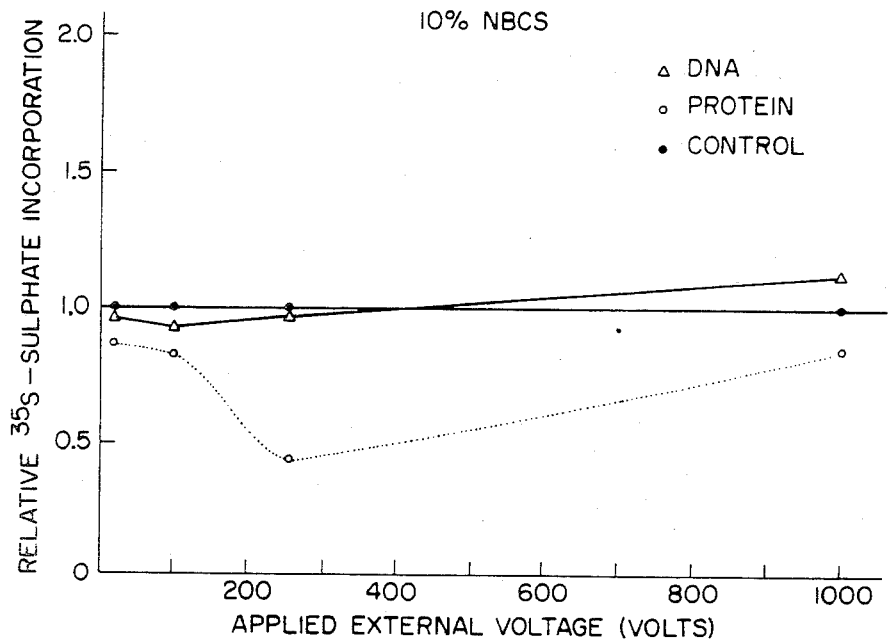

Articular cartilage for treatment according to the invention was obtained in a sterile manner from 1–2 week old male Holstein calf stifle joints. The cartilage thus obtained was placed in sterile cold Hank's Balanced Salt Solution and diced to slivers 1–2 mm thin, following which the diced specimens were rinsed with copious amounts of sterile cold Hank's solution.

The washed, diced cartilage pieces were placed in a modified Green Chamber and stirred in the presence of 10 mM EGTA CMF Hank's solution. All steps of matrix digestion were performed in 37° C., 5%CO$_2$, 98% humidity, and 21% O$_2$ incubation. Following a 10 minute exposure to low concentration EGTA, the specimen was then treated with multiple sequential enzymatic digestion of the matrix, sterile techniques being carefully observed at all times. The following enzymes and exposure times were used:

| (1) Trypsin .1% | 30 minutes |
| (2) Hyaluronidase .1% | 60 minutes |
| (3) Collagenase type II .2–.3% | 18–24 hours |

All enzymes were prepared in calcium-magnesium free (CMF) tissue culture media (TCM), except collagenase, which was prepared with 5 mM CaCl$_2$. The digesting cartilage was stirred intermittently (5 out of 20 minutes) at a rate of 60–120 rpm. It must be emphasized that sterility is crucial and that only a slow rate of stirring must be used or cellular viability will suffer significantly.

The following day, the cellular suspension in collagenase was aspirated with a sterile 50 ml syringe and placed in a sterile 250 ml Nalgene Polycarbonate flask. The cells were separated by centrifugation at 1800 rpm$\times$10 minutes. The cells were then retrieved and washed three times in cold Hank's solution. The cells were finally re-suspended in tissue culture media with 10% newborn calf serum. The cells were accurately counted using a hemocytometer and viability quantitated by trypan blue exclusion.

A cellular suspension of 2–2.5$\times$10$^6$ cells per ml was then prepared. Two mls. (4–5$\times$10$^6$ cells) were placed in 15 cc polystyrene conical test tubes, in which they were kept at 4° C. until pellet formation. Circular cellular pellets 2–3 mm in size were formed by centrifugation of the cellular suspension at 2000 rpms$\times$7 minutes. The pellets were incubated 24 hours at 37° C., 5%CO$_2$, 98% humidity, and 21% O$_2$ in the conical test tubes.

The following day, the pellets were transferred to 50 mm Falcon Petri dishes on a chick plasma clot. One to two drops of chick plasma and thrombin were placed in the bottom of the petri dish. The plasma thrombin was mixed and the pellets were placed on the clot with a sterile brush. One to two pellets were placed in a single petri dish. The pellets on the chick plasma clot were incubated for 30 minutes to allow the clot to gel. Then, three to four mls of tissue culture media with 10% newborn calf serum were added to the petri dishes and the pellets were left to incubate for 48 hours under standard conditions.

The tissue culture media with 10% newborn calf serum was aspirated sterilely and replaced with 15–17 mls of labelled tissue culture media with various newborn calf serum concentrations. $^{35}$S sulphate (10

μCi/ml) and $^3$H thymidine (5 μCi/ml) were used to measure proteoglycan formation and cellular replication, respectively. The large volume of labelled tissue culture media was necessary to assure that no air gap existed in the top of each petri dish. Grade A radioactive labels were used.

Six to seven petri dishes 10 (FIG. 1) were thus prepared containing chondrocyte pellets 11 and filled to the top with labelled tissue culture media 12. Each petri dish was sandwiched between a pair of metal electrodes 13 connected by wires 14 to a sine wave ultrasonic generator 15. A 60 khz sine wave signal at various voltages was applied to the electrodes 13 from the generator 15 for 24 hours. The voltages used were 10 V, 100 V, 250 V and 1000 V peak-peak. These voltages were externally applied and resulted in variable current densities in each dish (e.g., 250 V→40 μA/cm$^2$/dish). Assuming a constant impedance since the frequency remained constant, and linear proportionality between voltage and current, the 10 V signal corresponded to a current density of about 1.5 μA/cm$^2$ and the 1000 V signal corresponded to a current density of about 160 μA/cm$^2$; Two serum concentrations, 1% and 10% newborn calf serum, were used.

After having been stimulated electrically as described, the pellets were harvested and placed in individual dialysis bags, in which they were dialyzed against cold (4° C.) running tap water until the counts per minute (cpm) in the water were less than background. The pellets were then lypholyzed to dryness, following which they were hydrolyzed with 0.75 ml of 2N NaOH at 50° C. for 2-3 hours or until specimen solubilized. The solution was then neutralized with 0.75 ml 2N HCL.

A 1.0 ml specimen was used to measure deoxyribonuclein acid by the Abraham modification of the di- phenylamine-deoxyribose reaction (μg/ml). 0.1 ml was analyzed for protein using the Lowry micromethod with a bovine serum albumin standard (μg/ml). 0.1-0.2 ml of specimen was used for scintillation counting with an SL30 Liquid Scintillation Spectrometer. Counting was done for 10 minute intervals and results were expressed as cpm/μg DNA or cpm/μg protein. A group test was used to compare control and stimulated groups and a 5% significance level was applied in all statistical testing.

The numerical data obtained are summarized in Tables I-IV in which the numbers are the mean±one S.E. where n equals the number of runs. As shown in Table I, at 10 volts peak-peak, the externally applied (ie noninvasively) capacitively coupled field in 1% newborn calf serum (NBCS) decreased the thymidine counts per DNA by 44% (P<0.01). There was no significant change in thymidine counts per protein. In 10% NBCS, the same 10 volt peak-peak capacitively coupled field caused no significant change in thymidine counts per protein and per DNA. Sulphate counts per protein and per DNA were decreased significantly (P<0.01) in 1% NBCS and the 10 volt field. In 10% NBCS there was no statistical change.

TABLE I

| | | | Applied Voltage 10 Volts Peak-To-Peak | | | |
|---|---|---|---|---|---|---|
| | | | TCM with 1% NBCS | | TCM with 10% NBCS | |
| | | | cpm/ μg DNA | cpm/ μg protein | cpm/ μg DNA | cpm/ μg protein |
| $^{35}$S—sulfate incorporation | Control | | 1771 ±128 n = 11 | 226 ±18 n = 11 | 32261.5 ±1543.4 n = 12 | 2756.4 ±136.2 n = 12 |
| | Stimulation | | 1125 ±147 n = 12 (p < .01) | 154 ±18 n = 12 (p < 01) | 30962.8 ±1624.9 n = 12 N.S. | 2434.1 ±96.1 n = 12 N.S. |
| $^3$H—thymidine incorporation | Control | | 442 ±41 n = 10 | 39.7 ±2.1 n = 10 | 1849 ±124.9 n = 12 | 153.8 ±11.3 n = 12 |
| | Stimulation | | 202 ±14 n = 11 (p < .01) | 34.3 ±2.1 n = 11 N.S. | 1570.5 ±74.5 n — 12 N.S. | 129 ±9.0 n — 12 N.S. |

The 100 volt field (Table II) caused a 52% decrease in thymidine counts per DNA in 1% NBCS (P<0.01. Thymidine counts per protein were unchanged. In 10% NBCS, thymidine counts per protein and per DNA were unchanged. Sulphate counts were increased 15% and 18% in 1% NBCS for counts per DNA and per protein, respectively. However, there was no statistical difference when compared to controls (P$_{35}$>0.05). In 10% NBCS the 100 volt peak-to-peak field caused a 20% decrease in S$^{35}$ counts per protein (P<0.01) and no change in counts per DNA.

TABLE II

| | | | Applied Voltage 100 Volts Peak-to-Peak | | | |
|---|---|---|---|---|---|---|
| | | | TCM with 1% NBCS | | TCM with 10% NBCS | |
| | | | cpm/ μg DNA | cpm/ μg protein | cpm/ μg DNA | cpm/ μg protein |
| $^{35}$S—sulphate incorporation | Control | | 1771 ±128 n = 11 | 226 ±18 n = 11 | 32261.5 ±1543.4 n — 12 | 2756.4 ±136.2 n — 12 |
| | Stimulation | | 2030 ±231 n = 13 N.S. | 252 ±27 n = 13 N.S. | 31159.9 ±1342 n = 12 N.S. | 2226.4 ±80.3 n = 12 (p < .01) |
| | Control | | 442 ±41 n = 10 | 39.7 ±2.1 n = 10 | 1849.4 ±124.9 n = 12 | 153.8 ±11.3 n = 12 |

TABLE II-continued

| | | Applied Voltage 100 Volts Peak-to-Peak | | | |
|---|---|---|---|---|---|
| | | TCM with 1% NBCS | | TCM with 10% NBCS | |
| | | cpm/ µg DNA | cpm/ µg protein | cpm/ µg DNA | cpm/ µg protein |
| $^3$H—thymidine incorporation | Stimulation | 207 ±12 n = 12 (p < .01) | 35.1 ±1.2 n = 12 N.S. | 1899.9 ±133.6 n = 12 N.S. | 152.4 ±6.7 n = 12 N.S. |

The 250 volt peak-to-peak field caused the most dramatic results. In 1% NBCS (Table III) the thymidine counts per DNA were reduced by 53% (P<0.01). There was no change in counts per protein. In 10% NBCS there was a dramatic increase of 70% for $H^3$ counts per protein (P<0.05) and 80% for $H^3$ counts per DNA (P<0.05). In 1% NBCS, the sulphate counts per DNA were increased 86% (P<0$_3$501). $S^{35}$ counts per protein were increased 50% (P<0.01). There was no significant change in $S^{35}$ counts per DNA in 10% NBCS and the 250 volt peak-to-peak field.

sera (NBCS). These curves were generated by dividing the stimulation value (mean) by the control value (mean) at each voltage. This represents the relative effect and eliminates the necessity for explaining differences in total counts per minute usually due to the lot of radioactive label used. These figures appear to indicate that an optimum stimulatory "window" exists at about 250 volts peak-to-peak.

However, enhanced articular chondrocyte growth was experienced throughout a range of about 100 V to 900 V, corresponding to a current density range of about 15 $\mu A/cm^2$ to 145 $\mu A/cm^2$. Further, since a relatively low 1% serum concentration enhanced incorporation of H-thymidine, one would expect at least some enhanced incorporation of S-sulfate and/or H-thymidine using a serum concentration between 1% and 10%.

By subjecting articular chondrocytes to electrical stimulation in the manner described, their growth can be significantly enhanced.

TABLE III

| | | Applied Voltage 250 Volts Peak-To-Peak | | | |
|---|---|---|---|---|---|
| | | TCM with 1% NBCS | | TCM with 10% NBCS | |
| | | cpm/ µg DNA | cpm/ µg protein | cpm/ µg DNA | cpm/ µg protein |
| $^{35}$S—sulphate incorporation | Control | 21599 ±128 n = 8 | 3242 ±573 n = 8 | 30825 ±2101 n = 17 | 11251 ±2623 n = 17 |
| | Stimulation | 40385 ±3845 n = 10 (p < .01) | 4895 ±356 n = 10 (p < .05) | 29956 ±1469 n = 17 N.S. | 4615 ±455 n = 17 (p < .01) |
| $^3$H—thymidine incorporation | Control | 296 ±26 n = 8 | 32 ±3 n = 8 | 559 ±57 n = 16 | 50 ±8 n = 17 |
| | Stimulation | 246 ±24 n = 9 N.S. | 27 2 n = 9 N.S. | 914 ±99 n = 19 (p < .01) | 86 ±13 n = 18 (p < .05) |

The 1000 volt peak-to-peak field and 1% NBCS (Table IV) decreased the $H^3$ counts per DNA 47% (P<0.01). $H^3$ counts per protein were unchanged. In 10% NBCS there was no statistical change in $H^3$ counts per DNA or protein. $S^{35}$ counts were unchanged in 1% NBCS and the 100 volt peak-to-peak field. There was a 15% decrease in $S^{35}$ counts per protein (P<0.02) in 10% NBCS. $S^{35}$ counts per DNA were unchanged.

TABLE IV

| | | Applied Voltage 1000 Volts Peak-To-Peak | | | |
|---|---|---|---|---|---|
| | | TCM with 1% NBCS | | TCM with 10% NBCS | |
| | | cpm/ µg DNA | cpm/ µg protein | cpm/ µg DNA | cpm/ µg protein |
| $^{35}$S—sulphate incorporation | Control | 1771 ±128 n = 11 | 226 ±18 n = 11 | 32261.5 ±1543.4 n = 12 | 2756.4 ±136.2 n = 12 |
| | Stimulation | 1224 ±270 n = 9 N.S. | 170 ±31 n = 9 N.S. | 35685.1 ±3110.3 n = 12 N.S. | 2336.3 ±83 n = 12 (p < .02) |
| $^3$H—thymidine incorporation | Control | 442 ±23.1 n = 10 | 39.7 ±2.1 n = 10 | 1849.4 ±124.9 n = 12 | 153.8 ±11.3 n = 12 |
| | Stimulation | 234 ±11 n = 11 (p < .01) | 37.0 ±1.2 n = 11 N.S. | 1878.9 ±79.1 n = 13 N.S. | 140.3 ±5.0 n = 13 N.S. |

FIGS. 2–5 are dose response curves for the articular chondrocyte pellets in either 1% or 10% newborn calf The illustrative method and apparatus described above are susceptible of modification in form and detail within the scope of the following claims.

I claim:

1. A method of stimulating growth in articular chondrocytes comprising noninvasively subjecting said chondrocytes to an externally applied, capacitively coupled alternating current electric field having a frequency of about 60 KHz and at a current density in the range of about 15-145 μA/cm².

2. A method as defined in claim 1 in which the chondrocytes are subjected to an alternating current field at a current density of about 30–40 μamp/cm².

3. A method as defined in claim 2 in which the chondrocytes are subjected to the alternating current field in the presence of a low serum concentration.

4. A method as defined in claim 2 in which the chondrocytes are subjected to the alternating current field in the presence of a high serum concentration.

* * * * *